United States Patent
Rössler

(10) Patent No.: US 8,509,883 B2
(45) Date of Patent: Aug. 13, 2013

(54) METHOD FOR IDENTIFYING R WAVES IN AN ECG SIGNAL AND AN ECG MEASURING INSTRUMENT AS WELL AS A MAGNETIC RESONANCE DEVICE

(75) Inventor: Jürgen Rössler, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 90 days.

(21) Appl. No.: 13/166,837

(22) Filed: Jun. 23, 2011

(65) Prior Publication Data

US 2012/0004568 A1    Jan. 5, 2012

(30) Foreign Application Priority Data

Jun. 30, 2010   (DE) .......................... 10 2010 030 714

(51) Int. Cl.
*A61B 5/04* (2006.01)
(52) U.S. Cl.
USPC .......................................... 600/521; 600/509
(58) Field of Classification Search
USPC .................................................. 600/509, 521
See application file for complete search history.

(56) References Cited

U.S. PATENT DOCUMENTS

| | | | |
|---|---|---|---|
| 4,023,564 A * | 5/1977 | Valiquette et al. | 600/517 |
| 6,070,097 A | 5/2000 | Kreger et al. | |
| 6,944,495 B2 * | 9/2005 | MacAdam et al. | 600/521 |
| 8,380,285 B2 * | 2/2013 | Frank et al. | 600/413 |
| 2009/0318821 A1 * | 12/2009 | Demharter et al. | 600/509 |
| 2010/0191134 A1 | 7/2010 | Frank et al. | |

* cited by examiner

*Primary Examiner* — Christopher D Koharski
*Assistant Examiner* — Catherine Voorhees

(57) ABSTRACT

A method for identifying R waves in an ECG signal is proposed. An ECG measuring instrument measures ECG signals of a patient in which R waves are to be detected. The measured ECG signals are compared with respective reference quantities based on at least two comparison rules. The second comparison rule is dependent on a result of a first comparison conducted according to a first comparison rule. A signal that an R wave has been detected is issued if the first and the second comparison rules are fulfilled. Making the second comparison rule dependent on the result of the first comparison rule enables an adept response to changes of measurement conditions. These changes can be taken into account in further comparisons. Therefore the detection of R waves in an ECG signal can be optimized, leading to an improvement in the image quality in ECG-triggered MR examinations.

13 Claims, 3 Drawing Sheets

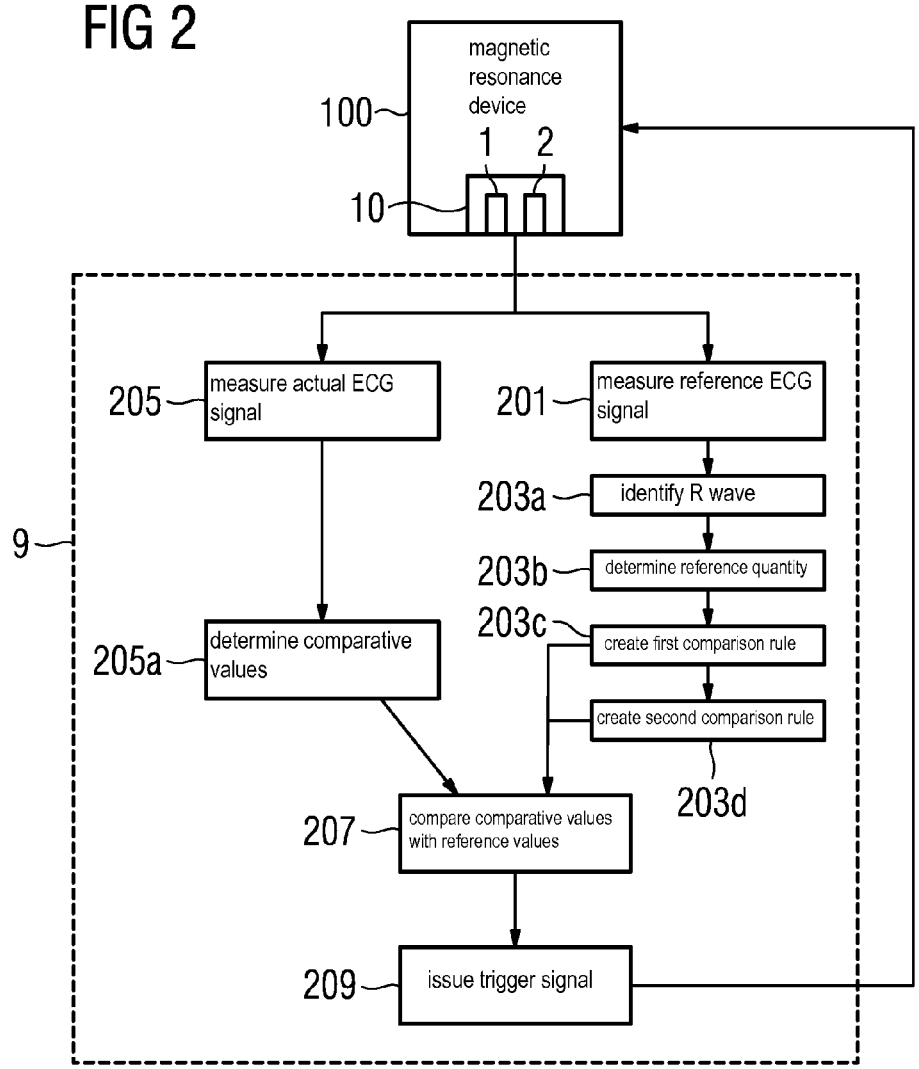
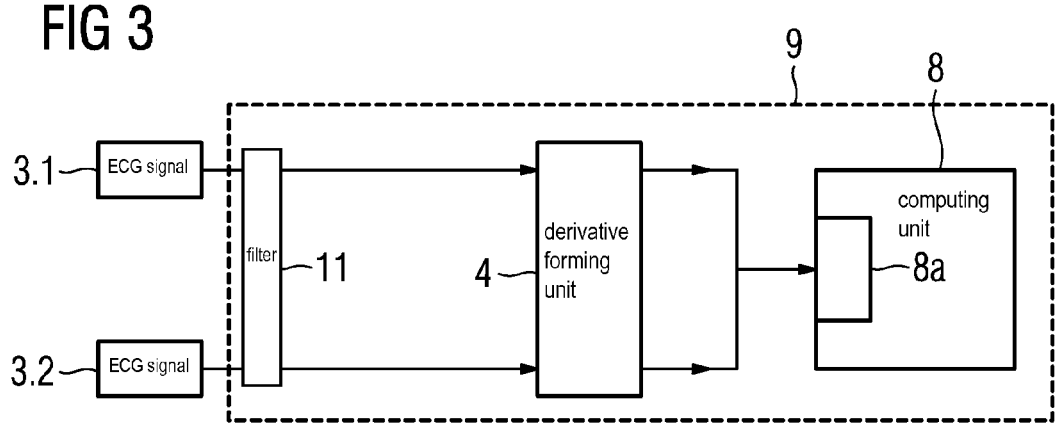

METHOD FOR IDENTIFYING R WAVES IN AN ECG SIGNAL AND AN ECG MEASURING INSTRUMENT AS WELL AS A MAGNETIC RESONANCE DEVICE

CROSS REFERENCE TO RELATED APPLICATIONS

This application claims priority of German application No. 10 2010 030 714.9 filed Jun. 30, 2010, which is incorporated by reference herein in its entirety.

FIELD OF THE INVENTION

The invention relates to a method for identifying R waves in an ECG signal, an ECG measuring instrument and a magnetic resonance device.

BACKGROUND OF THE INVENTION

ECG measuring instruments are primarily used for measuring and monitoring a patient's cardiac function, for which purpose the summation voltage of the electrical activity of the myocardial fibers is typically measured in the form of what is termed an "ECG signal" by way of at least two electrodes. An ideal waveform of such an ECG signal is shown by way of example in FIG. 1 as voltage U over time. According to Einthoven characteristic waveforms of the ECG signal are designated by the letters P, Q, R, S and T and generally reflect the different phases of a heartbeat.

There are other applications besides the pure monitoring of a patient's cardiac function. For example, ECG signals are also used in medical imaging applications for the purpose of generating trigger signals. Information about the cardiac cycle is acquired via the ECG signal during imaging in order thereby to synchronize the imaging with the cardiac activity. In particular in the case of imaging methods that require a relatively long acquisition time, high-quality images of the heart or images of regions that are moved by the heartbeat can be produced in this way.

ECG measuring instruments are also used for in-situ recording of ECG signals during an examination of a patient by means of a magnetic resonance device. In this case, however, operation in the magnetic resonance device imposes special requirements on the ECG measuring instrument due to the strong gradient fields and radio-frequency fields used there for the imaging in order to prevent mutual interference between magnetic resonance device and ECG measuring instrument. ECG measuring instruments that are magnetic-resonance-compatible in the aforementioned sense are available on the market.

Identifying R waves in ECG signals is essential for reliable triggering. Said identification is, however, made more difficult e.g. as a result of T-wave overshoots occurring in the magnetic field.

Magnetic fields that change over time, as used in the magnetic resonance device as magnetic gradient fields for position encoding, also continue to represent a further major problem in relation to reliable ECG signal measurement. According to the law of induction, temporally fluctuating magnetic fields of said type generate interference voltages which are coupled into the ECG signal recorded by the ECG electrodes as noise. Magnetically generated interference signals of said kind become superimposed on the ECG signal generated by the heart and distort said signal.

These sources of interference are extremely undesirable. Reliable detection of the R wave of the ECG signal is necessary in order to synchronize an acquisition of a magnetic resonance image with the heartbeat. The noise signals can be erroneously interpreted as an R wave e.g. due to their often similar shape and consequently can incorrectly initiate a triggering of an acquisition of a magnetic resonance image. On the other hand it can also happen that a "real" R wave is not detected as such due to the superimposed noise signals. This frequently leads to a significant deterioration in image quality.

Prior art attempts to solve these problems consisted in subjecting signals interpreted as a possible R wave to a simple threshold value check in addition prior to a triggering. Said threshold value check generally provides a maximum value that is not to be exceeded and a minimum value that is not to be undershot. If the maximum value is exceeded, it is assumed that a parasitic induction was present due to the gradient fields. If the minimum value is undershot, it is assumed that a T wave has erroneously been interpreted as an R wave. In both cases no trigger signal is issued.

Changes to the measurement conditions for the ECG measuring instrument represent a further difficulty. For example, in certain MR examinations it is necessary for the patient being examined to hold his/her breath for a certain time. This also affects the measured ECG signal, which can make it even more difficult to detect an R wave.

SUMMARY OF THE INVENTION

It is therefore the object of the invention to disclose a method, an ECG measuring instrument and a magnetic resonance device which permit reliable detection of R waves of ECG signals measured in the magnetic resonance device even under changed measurement conditions.

The object is achieved according to the invention a method a, an ECG measuring instrument and a magnetic resonance device as claimed in the claims.

A method according to the invention for identifying R waves in an ECG signal comprises the following steps:
  using an ECG measuring instrument to measure ECG signals of a patient in which R waves are to be detected,
  comparing values of the measured ECG signals corresponding to reference quantities with the respective reference quantities on the basis of at least two comparison rules, the second comparison rule being dependent on a result of a first comparison conducted according to a first comparison rule,
  issuing a signal that an R wave has been detected if at least the first and the second comparison rule are fulfilled.

Making the second comparison rule dependent on the result of the first comparison rule enables an adept response to be made to changes in the measurement conditions which affect the result of the first comparison rule and these changes can be taken into account in addition in further comparisons. In this way the detection of R waves in a measured ECG signal can be optimized, leading in turn to an improvement in the image quality in ECG-triggered MR examinations.

In an embodiment variant of the invention, in a comparison using a comparison rule a reference quantity is at least one complex number whose real part is the time derivative of a reference signal value of a first channel of an ECG measuring instrument and whose imaginary part is the time derivative of a reference signal value of a second channel of the ECG measuring instrument, the reference signal values of the first and second channel each having been measured at the same time instant. Said reference quantity is compared with a corresponding quantity, i.e. a complex number whose real part is the time derivative of a current signal value of the first channel of the ECG measuring instrument and whose imaginary part is the time derivative of a current signal value, measured at the same time instant, of the second channel of the ECG measuring instrument. The first time derivative of a signal can be determined without great effort and already permits meaningful comparisons to be made, in particular in the case of ECG signals.

A possible first comparison rule includes the use of an optimal filter and output of a similarity value as result. Similarity values express the correlation between the compared quantities and consequently are particularly suitable for identifying identical patterns. Since the ECG signal and also its time derivative have a periodic pattern, the signal is suitable for analysis using optimal filters.

A possible second comparison rule includes determining a deviation of the reference quantity from a corresponding quantity of the measured ECG signal multiplied by a factor that is dependent on the similarity value, wherein the deviation is established in particular by way of the determination of an error, in particular the sum of the error squares. Determining a deviation of a reference value and a current value that is made dependent on a similarity value permits the degree of similarity to be taken into account in the comparison. In contrast to a direct comparison of two values without further dependence on similarity values, a systematic change can therefore be detected and taken into account.

An ECG measuring instrument according to the invention comprises a processing unit, a computing unit and a memory unit for performing a method according to the invention.

A magnetic resonance device according to the invention comprises an ECG measuring instrument, a processing unit, a computing unit and a memory unit for performing a method according to the invention, wherein the issued trigger signal is used for triggering measurements by means of the magnetic resonance device.

The method-related advantages apply analogously to an ECG measuring instrument according to the invention and a magnetic resonance device according to the invention.

BRIEF DESCRIPTION OF THE DRAWINGS

Further advantages and details of the present invention will emerge from the exemplary embodiments described herein below as well as with reference to the drawings. The examples presented constitute no limitation of the invention. In the drawings:

FIG. 2 is a schematic representation of an execution sequence of the method according to the invention in conjunction with an ECG measuring instrument and a magnetic resonance device, FIG. 3 schematically shows an ECG measuring instrument.

DETAILED DESCRIPTION OF THE INVENTION

Figure 1:
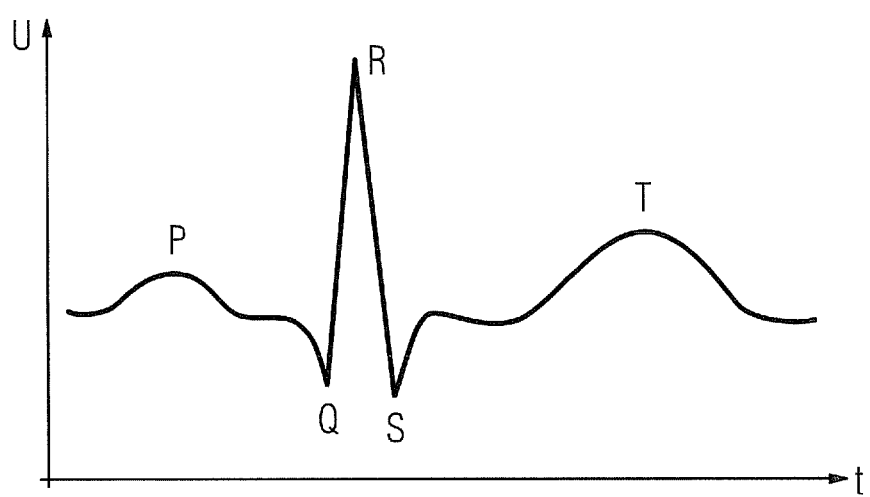
FIG. 1 shows by way of example an ideal waveform of an ECG signal over time.

The method according to the invention in conjunction with an ECG measuring instrument and a magnetic resonance device is explained below with reference to FIGS. 2 and 3.

During an examination a patient having an attached ECG measuring instrument 10 is positioned in the magnetic resonance device 100. The magnetic resonance device 100 and the ECG measuring instrument are in this case represented merely schematically as a block, since the basic layout consisting of magnet unit, radio-frequency coils, gradient coil unit, patient couch, and control units of a magnetic resonance device is well-known, as also is the basic layout of an ECG measuring instrument comprising ECG electrodes and amplifier/filter units for measuring a voltage between two ECG electrodes.

According to the invention the magnetic resonance device 100 comprises in particular an ECG measuring instrument 10, a processing unit 9, a computing unit 8 and a memory unit 8a. The separate or combined representation of said units is to be understood not necessarily physically, but rather as a separation or combination based on meaningful entities.

The ECG measuring instrument 10, the processing unit 9, the computing unit 8 and the memory unit 8a are connected to the magnetic resonance device 100 and to one another for the purpose of transmitting data.

The ECG measuring instrument 10 is represented as comprising two ECG channels 1 and 2. The method according to the invention can also be performed using ECG measuring instruments having more than two ECG channels, although, as will be explained in greater detail below, two ECG channels are already sufficiently suitable for a particularly reliable identification of R waves in ECG signals with little effort.

In such an arrangement one ECG channel 1,2 outputs an ECG signal which the ECG measuring instrument determines from a voltage between two ECG electrodes (not shown) attached to the patient.

In an advantageous embodiment variant, in a first step 201 one reference ECG signal is measured at each of the channels 1 and 2 of the ECG measuring instrument 10. In this case the reference ECG signals are advantageously recorded in an environment that is not disrupted by external influences, e.g. in the magnet of the magnetic resonance device 100, without gradient fields being switched on in the magnetic resonance device 100. In a further step 203a, the R wave is identified in each reference ECG signal, e.g. in one of the ways known in the prior art.

Next (step 203b), there is determined from the reference ECG signals at least one reference quantity which the reference ECG signal assumes in a time interval which advantageously starts before the R wave of the ECG signal and lasts at a maximum up to the time of the occurrence of the R wave. Thus, the reference quantity can also be a variation of a quantity determined from the ECG signal over a period of time in the time interval. The reference quantity can also be determined in some other way, although by means of such a determination of the reference quantity it can be ensured that the reference quantity can be compared particularly effectively with an ECG signal measured later on the same patient by means of the same ECG measuring instrument, since a great similarity is to be expected between the reference ECG signals and the subsequently measured current ECG signals.

In this case the size of the time interval can be specified with a large degree of freedom.

In an advantageous exemplary embodiment, the time interval lies e.g. within the rise of the ECG signal between the points designated by "Q" and "R" (see FIG. 1). If more than one ECG channel 1,2 is recorded, the time interval advantageously begins as soon as the start of the rise between "Q" and "R" is detected in one of the channels 1,2, and ends as soon as the end of said rise is detected in the last of the channels 1,2. This means that the time interval has a duration in the order of approx. 12 to 20 milliseconds, max. 50 to 60 milliseconds, before the R wave. With such a choice of time interval, the further analysis of ECG signals within the time interval can be effectively accomplished owing to the particularly distinctive signal waveform there, e.g. owing to a relatively large amplitude there and a relatively large first derivative of the signal waveform there, as described below.

In this case a reference quantity can be determined e.g. as illustrated schematically in FIG. 3. The ECG signals 3.1 and 3.2 acquired from the channels 1 and 2 are supplied to a processing unit 9 which is embodied for the purpose of further processing the ECG signals. Thus, on the one hand the ECG signal 3.1,3.2, provided it lies in the time interval, can be stored as a possible reference quantity in a memory unit 8a as it was supplied to the processing unit 9. The reference quantity is therefore simply a signal value over time, i.e. a signal waveform, of a channel of the ECG measuring instrument. Where appropriate, instead of the entire variation of the ECG signal 3.1,3.2 in the time interval being stored as a reference quantity, only parts of the same will be stored, e.g. individual measurement points in the time characteristic. Basically, however, maximally comprehensive signal waveforms from the time interval are to be preferred as a more reliable reference quantity over individual measurement points if only on account of the greater volume of data and the averaging over the data that is possible thereby. Furthermore, such an averaging can also be performed over a plurality of recorded signal waveforms of reference ECG signals.

An ECG signal 3.1,3.2 in the processing unit 9 is advantageously supplied to a derivative forming unit 4 which forwards the time derivative of the respective ECG signal 3.1,3.2 as a reference quantity to the memory unit 8a. Storing said time derivative as a reference quantity is possible in addition or alternatively to the storing of the ECG signal 3.1,3.2 itself as a reference quantity. In this case, in addition to a first time derivative of the respective ECG signal 3.1,3.2, a second time derivative of the respective ECG signal 3.1,3.2 can also be calculated by the derivative forming unit 4 and forwarded to the memory unit 8a.

An advantage of the use of the respective first and, where applicable, second time derivatives of the described quantities is that these are not subject to possible offset fluctuations.

In further steps a first comparison rule (203c) and a second comparison rule (203d) are created from the stored reference quantities. This happens in a computing unit 8 which has access to the reference quantities stored in the memory unit 8a and to which subsequently measured ECG signals can be routed, in processed form if necessary. As their result the comparison rules specify how subsequently measured ECG signals in which an R wave is to be identified must correlate with the reference quantities when an R wave is present.

A first comparison rule can include the use of an optimal filter and output of a similarity value as result. An optimal filter, also referred to as a "matched filter" (MF), determines the similarity of a curve, in this case e.g. of the waveform of the subsequently measured ECG signal or of a value of the ECG signal corresponding to a reference quantity in the time interval, in this case $\Delta t$, as a comparative value, with a predefined curve, in this case a reference quantity, e.g. the waveform of the first time derivative of the reference ECG signals. Mathematically, this advantageously happens through forming of the correlation between reference quantity and corresponding quantity, e.g. advantageously according to the following formula:

$$MF(\tau) = \alpha \cdot \sum_{t=0}^{\Delta t} X(\tau - \Delta t + t) \cdot LX^*(t),$$

where LX(t) is the reference quantity, X(t) is the measured corresponding comparative value, each of which is represented as a complex-value quantity, $\Delta t$ is the time interval, and $\alpha$ is a normalization factor which ensures that MF($\tau$) is equal to one if X(t) is identical to the previously determined reference quantity LX($\tau$). As is customary with complex numbers, the "*" signifies that the conjugate-complex quantity is used. An advantageous choice of the normalization factor is the reciprocal sum of the squared reference quantity values over the time interval. This value can also be described as the "energy" of the reference quantity in the time interval.

A positive result of said comparison criterion is therefore a comparative value equal to one (ideal value) or a value which deviates from one at a maximum by a predefinable small threshold value $\epsilon_U$ downward or $\epsilon_O$ upward. In this case the upper and lower threshold $\epsilon_O$ and $\epsilon_U$, respectively, can be chosen according to the desired precision.

Figure 4:
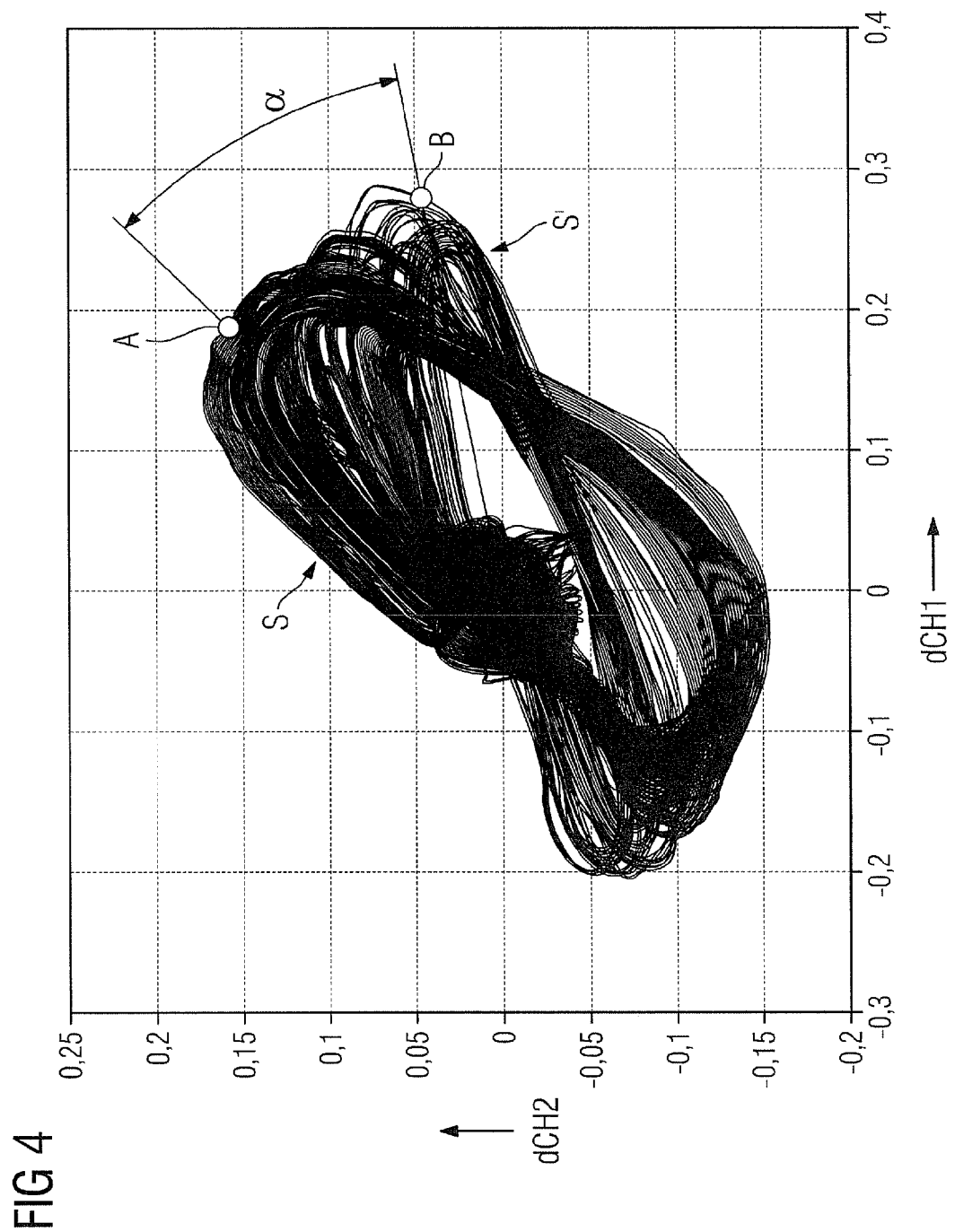
FIG. 4 shows an exemplary trajectory of the first time derivative of signal waveforms of two ECG signals under a change in the measurement conditions.

It has been shown that changes in the measurement conditions cause changes in the measured ECG signals and consequently also in quantities derived from the measured ECG signals. An example is shown in FIG. 4, where a trajectory of the first time derivative of an ECG signal (dCH1) measured at a first channel of an ECG measuring instrument is plotted against the first time derivative of an ECG signal (dCH2) measured at a second channel of the ECG measuring instrument. As can be seen, the trajectory includes a large loop S on which the point A marks an R wave which, following entry of the change in the measurement conditions, in this case a change in the patient's breathing, is tilted by an angle $\alpha$ and now runs in the loop S', as a result of which an R wave is now represented by the point B. Points A and B can thus be transferred into one another by way of a rotation through the angle $\alpha$.

If the reference quantity "first time derivative of the ECG signal" was determined in this case prior to the change in the measurement conditions, then it is expected that an R wave will be present again when the time derivative of the current ECG signal lies on the point A and the R waves lying on point B after the change will no longer be detected properly.

The comparison of such a reference quantity with such a current corresponding value with the above optimal filter yields, not the ideal value one ("1"), but exp(i*−α)), where i is the so-called imaginary unit, i.e. i=$\sqrt{-1}$.

In order nonetheless to obtain a positive result of the optimal filter comparison criterion in this case, instead of the above requirement for the comparative value to be directly equal to one (ideal value) or a value that deviates at a maximum by a predefinable small threshold value $\epsilon_U$ downward or $\epsilon_O$ upward from one, it can be required that the amount of the above comparative value, i.e. |MF($\tau$)|, fulfills this requirement, since |exp(i*R)|=1, for all real numbers R. In this case the first comparison rule therefore includes the use of an optimal filter and output of the amount of a similarity value as result.

Alternatively or in addition it can be required, for a positive result of the comparison, that the angle $\alpha$ shall not exceed an upper limit $\alpha\_o$ and shall not fall below a lower limit $\alpha\_u$. If the angle determined using the optimal filter is too great, this indicates in turn that no R wave is in fact present, since the changes in the ECG signal due to the changes in the measurement conditions are usually not serious ones.

In step 203d, a second comparison rule can now be applied which includes determining a deviation of the reference quantity from a corresponding quantity of the measured ECG signal multiplied by a factor that is dependent on the similarity value. This can advantageously take place in that the reference quantities are processed in such a way that e.g. the sum over the error squares of quantities of the measured ECG signal corresponding to the reference quantities multiplied by exp(i*β) is determined with respect to the reference quantities. The sum of the error squares is accordingly determined e.g. via the following formula:

$$SumQ(\tau) = \alpha_S \cdot \sum_{t=0}^{\Delta t} (|X(\tau - \Delta t + t) \cdot \exp(i \cdot \beta) - LX(t)|)^2,$$

where LX(t) is the reference quantity (time derivative of the reference ECG signal), X(t) is the measured corresponding comparative quantity, Δt is the time interval, and $\alpha_S$ is a normalization factor which ensures that SumQ(τ) is equal to zero if X(t)*exp(i*β) is identical to the previously determined reference quantity LX(τ). In this example the measured ECG signal is therefore multiplied by a factor that is dependent on the similarity value, a complex number exp(i*β). In this case the argument β of the complex number in its exponential exp(i*β) is advantageously dependent for example as follows on the angle α defined by the similarity value, and hence on the similarity value: β=α can be set if the angle α does not exceed an upper limit α_o and does not fall below a lower limit α_u and otherwise β=0. The result of this is that in the case of small tilts of the trajectory the comparison via a deviation also takes said tilting into account, but in the case of excessively large tilts, which indicate that in fact no R wave is present, a "normal" comparison is performed, without taking into account possible tilts (exp(i·0)=1).

In this case an advantageous choice of the normalization factor is once again the reciprocal sum of the squared reference quantity values over the time interval. This value can also be referred to as the "energy" of the reference quantity in the time interval.

A positive result of this comparison criterion is therefore a value equal to zero (ideal value) or a value which deviates from zero at a maximum by a predefinable small threshold value ε.

Another type of error calculation, such as e.g. determining the simple error, for deter wining the deviation is likewise conceivable, depending on the desired precision. The respective advantages and disadvantages of different error calculations are well-known.

A measurement of a reference ECG signal and the steps up to the formulation of the comparison rules (201, 203a,b,c,d) are advantageously performed each time after the ECG measuring instrument 10 is attached to the patient before the planned measurements by means of the magnetic resonance device 100 and requiring triggering are performed. In particular a reference ECG signal is repeatedly measured after the ECG measuring instrument 10 is attached to the patient positioned on an examination couch of the magnetic resonance device until such time as the patient and with him/her the ECG measuring instrument 10 are disturbed by the electromagnetic fields of the magnetic resonance device 100. In this way it is possible to determine particularly up-to-date reference quantities after the contacting of the ECG measuring instrument 10 with the patient has been stabilized to the greatest possible extent and no disrupting interference effects of the magnetic field of the magnetic resonance device on the ECG measuring instrument 10 are as yet present.

Further comparison rules, such as e.g. comparisons of magnitudes or angles determined as reference quantities from the reference signal with corresponding magnitudes and angles of the current ECG signal, are conceivable which can be interrogated in parallel in order to make the detection of the R wave by means of the thus even stronger checking of the current ECG signal even more reliable. Storing a plurality of reference quantities and using them for creating comparison rules also increases the flexibility and stability of the method. It may, however, also suffice to evaluate only one reference quantity, e.g. the time derivative, in particular the first time derivative of the ECG signal values.

Once the reference quantities are known and the comparison rules have been specified, the actual ECG measurement that is intended to be used for triggering further measurements or examinations, e.g. by means of the magnetic resonance device, is started (step 205). From the ECG signals measured during this process, comparative values corresponding to the reference quantities are determined analogously to the procedure for determining the reference quantities described with reference to FIG. 3 (step 205a).

These comparative values (e.g. first time derivative of the signal values) are compared with the reference values on the basis of at least one first comparison rule and one second comparison rule that is dependent on a result of the first comparison rule (step 207).

Furthermore advantageously, prior to the determination of the comparative values (cf. FIG. 3) reference ECG signals and ECG signals measured prior to the determination of the reference quantities are supplied to a smoothing filter 11, for example a lowpass filter, which cleans the ECG signals e.g. of high-frequency interference. Using "smoothed" reference values and comparative values obtained in this way, the above-described steps 203c,207 and 209 can be performed analogously, in particular in addition.

A condition for the issuing of a trigger signal can be that both the results of the above-described comparison with the unsmoothed values and the results of said "smoothed" comparison must be positive (conjunctive function; "AND"); alternatively, the results of the two comparisons can be drawn upon using a disjunctive function ("OR") as a condition for the issuing of a trigger signal.

Using such a smoothing filter 11 does in fact lengthen the duration of the method overall. The disadvantage of this longer duration, which lies in the order of approx. 2 to 3 milliseconds, must if necessary be weighed against the advantage of having interference-free signals for the evaluation.

If at least the results of the first and second comparison rule are positive, in a final step 209 a trigger signal is issued which is supplied to the magnetic resonance device and there triggers a measurement, e.g. an acquisition of an image of an organ.

Other conditions that must be fulfilled before a trigger signal is issued are conceivable as a further measure to avoid triggering errors. Thus, for example, it can be required that the issuing of a trigger signal in step 209 takes place only if in addition, following confirmation of a sufficient number of positive results of the already described criteria, the first time derivative of at least one measured ECG signal value deviates at a maximum only by a small, predefinable threshold value from zero. The existence of an extreme value in the measured signal waveform is identified by means of such an extreme condition. In this way the time instant at which an R wave is present, since at that point such an extreme value, a maximum, is present, can be determined particularly precisely, and consequently the trigger signal can be issued particularly precisely.

As a further condition for the issuing of a trigger signal, e.g. also in the case described in the last paragraph, a trigger signal can be released only if a predefinable maximum duration between a confirmation of a sufficient number of positive results on the one hand and the identification of an extreme value in the measured signal on the other hand is not exceeded. Such a maximum duration is advantageously less than or equal to the already described time interval, particularly advantageously in the order of approx. 15 milliseconds.

The invention claimed is:

1. A method for issuing a trigger signal for a magnetic resonance device, comprising:
   measuring a reference ECG signal of a patient in an environment without being disturbed by an gradient field of the magnetic resonance device using an ECG measuring instrument;
   identifying an R wave in the reference ECG signal using a processing unit;
   determining a reference quantity from the reference ECG signal in a time interval starting before the R wave and lasting maximum up to an occurrence of the R wave using the processing unit;
   measuring an ECG signal of the patient in an environment being disturbed by the gradient field of the magnetic resonance device using the ECG measuring instrument;
   creating a first comparison rule from the reference quantity comprising an optimal filter and outputting a similarity value using the processing unit;
   comparing the measured ECG signal with the reference quantity based on the first comparison rule;
   creating a second comparison rule comprising determining a deviation of the reference quantity from the measured ECG signal multiplied by a factor using the processing unit, wherein the factor is dependent on the similarity value of the first comparison rule;
   comparing the measured ECG signal with the reference quantity based on the second comparison rule; and
   issuing the trigger signal for the magnetic resonance device if results of the comparison based on the first and the second comparison rules are positive.

2. The method as claimed in claim 1,
   wherein the reference quantity is a complex number,
   wherein a real part of the complex number is a time derivative of a reference signal value of a first channel of the ECG measuring instrument, and
   wherein an imaginary part of the complex number is a time derivative of a reference signal value of a second channel of the ECG measuring instrument at a same time.

3. The method as claimed in claim 1,
   wherein the reference quantity is a chronological sequence of complex numbers,
   wherein real parts of the complex numbers are time derivatives of reference signal values of a first channel of the ECG measuring instrument, and
   wherein imaginary parts of the complex numbers are time derivatives of reference signal values of a second channel of the ECG measuring instrument at a same time.

4. The method as claimed in claim 1, wherein the factor is a complex number $\exp(i*\beta)$, wherein $\beta$ is dependent on an angle $\alpha$ defined by the similarity value.

5. The method as claimed in claim 4, wherein $\beta$ equals to $\alpha$ if $\alpha$ does not exceed an upper limit and does not fall below a lower limit.

6. The method as claimed in claim 4, wherein $\beta$ equals to zero if $\alpha$ exceeds an upper limit or falls below a lower limit.

7. The method as claimed in claim 1, wherein the deviation is determined by an error.

8. The method as claimed in claim 7, wherein the deviation is determined by a sum of the error squares.

9. The method as claimed in claim 1, wherein the first comparison rule comprises a positive result if an absolute value of the similarity value does not exceed an upper limit and does not fall below a lower limit and/or an angle defined by the similarity value does not exceed a further upper limit and does not fall below a further lower limit.

10. The method as claimed in claim 1, wherein the second comparison rule has a positive result if the deviation does not exceed a threshold.

11. The method as claimed in claim 1, wherein the reference quantity is an ECG signal measured on the patient by the ECG measuring instrument at a different time.

12. An ECG measuring instrument, comprising:
    an ECG channel for measuring:
       a reference ECG signal of a patient in an environment without being disturbed by an gradient field of a magnetic resonance device, and
       an ECG signal of the patient in an environment being disturbed by the gradient field of the magnetic resonance device; and
    a processing unit adapted to:
       identify an R wave in the reference ECG signal;
       determine a reference quantity from the reference ECG signal in a time interval starting before the R wave and lasting maximum up to an occurrence of the R wave using the processing unit;
       create a first comparison rule from the reference quantity comprising an optimal filter and outputting a similarity value using the processing unit;
       compare the measured ECG signal with the reference quantity based on the first comparison rule;
       create a second comparison rule comprising determining a deviation of the reference quantity from the measured ECG signal multiplied by a factor using the processing unit, wherein the factor is dependent on the similarity value of the first comparison rule;
       compare the measured ECG signal with the reference quantity based on the second comparison rule; and
       issuing a trigger signal for the magnetic resonance device if results of the comparison based on the first and the second comparison rules are positive.

13. A magnetic resonance device, comprising:
    an ECG measuring instrument for measuring:
       a reference ECG signal of a patient in an environment without being disturbed by an gradient field of the magnetic resonance device, and
       an ECG signal of the patient in an environment being disturbed by the gradient field of the magnetic resonance device; and
    a processing unit adapted to:
       identify an R wave in the reference ECG signal;
       determine a reference quantity from the reference ECG signal in a time interval starting before the R wave and lasting maximum up to an occurrence of the R wave using the processing unit;
       create a first comparison rule from the reference quantity comprising an optimal filter and outputting a similarity value using the processing unit;
       compare the measured ECG signal with the reference quantity based on the first comparison rule;
       create a second comparison rule comprising determining a deviation of the reference quantity from the measured ECG signal multiplied by a factor using the processing unit, wherein the factor is dependent on the similarity value of the first comparison rule;
       compare the measured ECG signal with the reference quantity based on the second comparison rule; and issue a trigger signal for the magnetic resonance device if results of the comparison based on the first and the second comparison rules are positive.

* * * * *